United States Patent [19]

Dalla-Favera et al.

[11] Patent Number: 5,641,672
[45] Date of Patent: Jun. 24, 1997

[54] CLONING AND USES OF THE GENETIC LOCUS BCL-6

[75] Inventors: Riccardo Dalla-Favera; Raju S. K. Chaganti, both of New York, N.Y.

[73] Assignees: The Trustees of Columbia University in the City of New York; Sloan-Kettering Institute for Cancer Research, both of New York, N.Y.

[21] Appl. No.: 74,967

[22] Filed: Jun. 9, 1993

[51] Int. Cl.⁶ .......................... C12N 15/12; C12N 15/79; C12N 15/70

[52] U.S. Cl. ................ 435/325; 435/252.3; 435/320.1; 435/348; 435/365; 435/367; 435/364; 536/23.5; 536/24.31

[58] Field of Search .................. 536/23.5, 24.31; 435/69.1, 240.1, 252.3, 320.1

[56] References Cited

U.S. PATENT DOCUMENTS

| | | | |
|---|---|---|---|
| 5,015,568 | 5/1991 | Tsujimoto et al. | 435/5 |
| 5,149,628 | 9/1992 | Croce | 435/6 |

OTHER PUBLICATIONS

Van Cong et al "The human homologues of Fim1, Fim2/c–Fms, and Fim3,. . . " *Hum Genet.* 81(3):257–263 (Feb. 1989).

Ye et al "Cloning of bcl–6. . . " *Cancer Res.* 53:2732–2735 (15 Jun. 1993).

Rosati et al "Members of the Zinc finger protein gene family . . . " *Nuc. Acids Res.* 19(20):5661–5667 (Oct. 1990).

Baron et al "Identification of the gene associated with the recurring chromosomal translocations t(3:14)(q27;q32) . . . " *PNAS* 90:5262–5266 (Jun. 1993).

Cleary et al "Nucleotide sequence of a t(14;18) chromosomal breakpoint in follicular lymphoma . . . " *PNAS* 82:7439–7443 (Nov. 1985).

Bastard, C., et al. (1992) Translocations involving band 3q27 and Ig gene regions in non–Hodgkin's lymphoma. *Blood*, 79:2527–2531. (Exhibit B).

Offit, K., et al. (1989) A novel translocation associated with diffuse non–Hodgkin's lymphoma. *Blood*, 74:1876–1879. (Exhibit C).

*Primary Examiner*—Stephen G. Walsh
*Attorney, Agent, or Firm*—John P. White

[57] ABSTRACT

This invention provides an isolated vertebrate nucleic acid molecule the bcl-6 locus. This invention also provides an isolated human nucleic acid molecule of bcl-6 locus. This invention further provides a nucleic acid molecule comprising a nucleic acid molecule of at least 15 nucleotides capable of specifically hybridizing with a sequence included within the sequence of the nucleic acid molecule of bcl-6 locus. This invention provides an isolated vertebrate nucleic acid molecule of bcl-6 operatively linked to a promoter of RNA transcription. This invention provides a vector which comprises the nucleic acid molecule of bcl-6 locus. This invention provides a host vector system for the production of a polypeptide encoded by bcl-6 locus, which comprises the vector of bcl-6 locus in a suitable host. This invention provides a polypeptide encoded by the isolated vertebrate nucleic acid molecule of bcl-6 locus. This invention provides an antibody capable of binding to polypeptide encoded by bcl-6 locus. Finally, this invention provides a method of diagnosing diffuse-type B-cell lymphoma in a subject which comprises detecting nucleic acid molecule of bcl-6 locus in a sample from a subject.

16 Claims, 15 Drawing Sheets

FIGURE 2
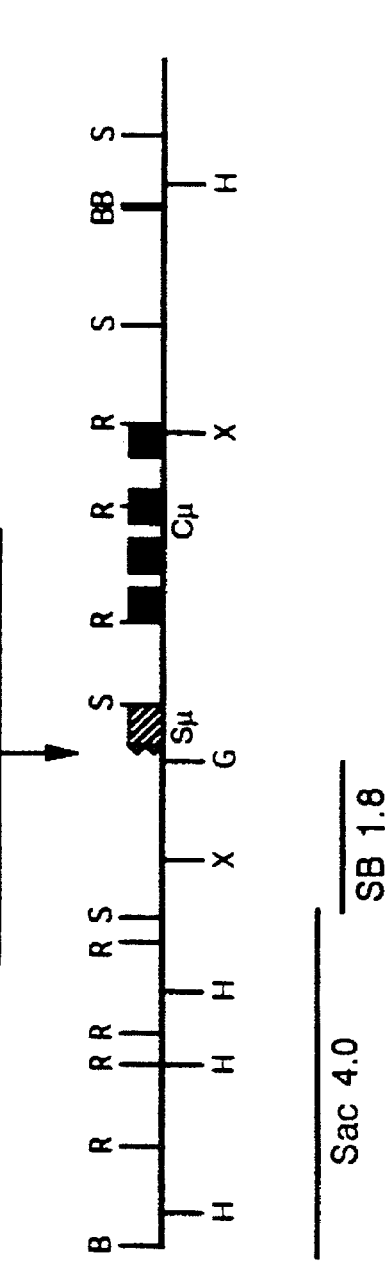
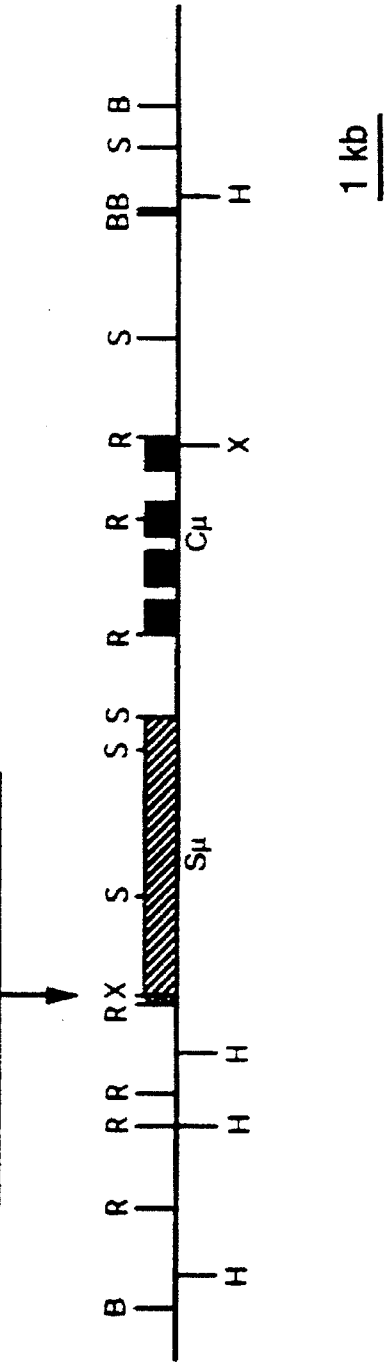

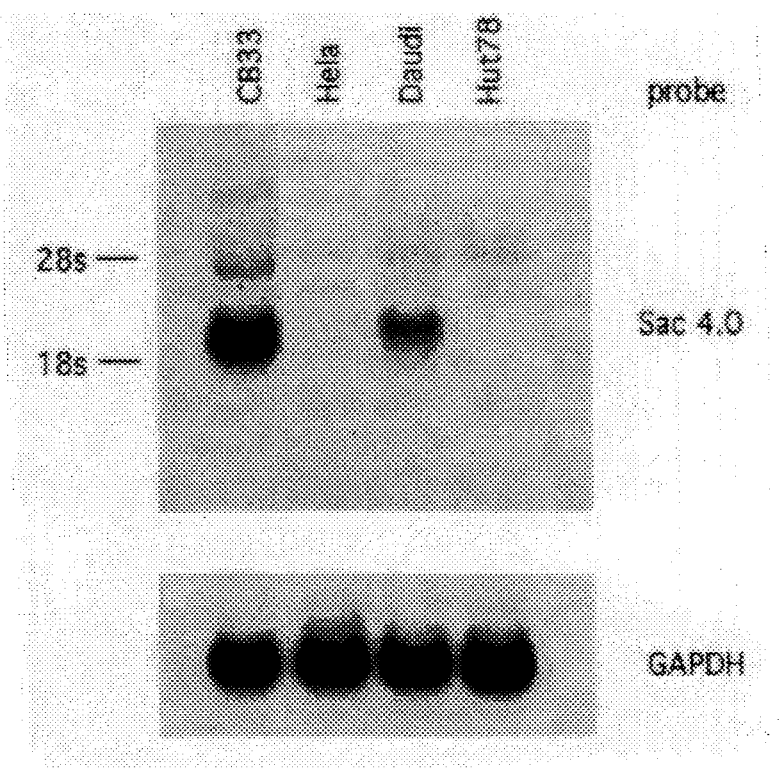

Lambda-SM71 = a recombinant Lambda phage clone containing Bcl-6 breakpoint
H = Hind III
R = EcoR I
S = Sac I
X = Xho I

FIGURE 9A

```
GGCCCCTCGA GCCTCGAACC GGAACCTCCA AATCCGAGAC GCTCTGCTTA TGAGGACCTC         60
GAAATATGCC GGCCAGTGAA AAAATCTTAT GGCTTTGAGG GCTTTTGGTT GGCCAGGGGC        120
AGTAAAAATC TCGGAGAGCT GACACCAAGT CCTCCCCTGC CACGTAGCAG TGGTAAAGTC        180
CGAAGCTCAA ATTCCGAGAA TTGAGCTCTG TTGATTCTTA GAACTGGGGT TCTTAGAAGT        240
GGTGATGCAA GAAGTTTCTA GGAAAGGCCG GACACCAGGT TTGAGCAAAA ATTTTGGACT        300
GTGAAGCAAG GCATTGGTGA AGACAAA ATG GCC TCG CCG GCT GAC AGC TGT            351
                              Met Ala Ser Pro Ala Asp Ser Cys
                               1               5

ATC CAG TTC ACC CGC CAT GCC AGG GAT GTT CTC AAC CTT AAT CGT               399
Ile Gln Phe Thr Arg His Ala Arg Asp Val Leu Asn Leu Asn Arg
         10                  15                  20

CTC CGG AGT CGA GAC ATC TTG ACT GAT GTT GTC ATT GTT GTG AGC CGT           447
Leu Arg Ser Arg Asp Ile Leu Thr Asp Val Val Ile Val Val Ser Arg
 25                  30                  35                  40

GAG CAG TTT AGA GCC CAT AAA ACG GTC CTC ATG GCC TGG AGA GGC CTG           495
Glu Gln Phe Arg Ala His Lys Thr Val Leu Met Ala Trp Arg Gly Leu
             45                  50                  55

TTC TAT AGC ATC TTT ACA GAC CAG TTG AAA TGC AAC CTT AGT GTG ATC           543
Phe Tyr Ser Ile Phe Thr Asp Gln Leu Lys Cys Asn Leu Ser Val Ile
                 60                  65                  70

AAT CTA GAT CCT GAG ATC AAC CCT GAG GGA TTC TGC ATC CTC CTG GAC           591
Asn Leu Asp Pro Glu Ile Asn Pro Glu Gly Phe Cys Ile Leu Leu Asp
         75                  80                  85
```

FIGURE 9B

```
TTC ATG TAC ACA TCT CGG CTC AAT TTG CGG GAG GGC AAC ATC ATG GCT    639
Phe Met Tyr Thr Ser Arg Leu Asn Leu Arg Glu Gly Asn Ile Met Ala
     90                      95                     100

GTG ATG GCC ACG GCT ATG TAC CTG CAG ATG GAG CAT GTT GAC ACT        687
Val Met Ala Thr Ala Met Tyr Leu Gln Met Glu His Val Asp Thr
    105                     110                     115        120

TGC CGG AAG TTT ATT AAG GCC AGT GAA GCA GAG ATG GTT TCT GCC ATC    735
Cys Arg Lys Phe Ile Lys Ala Ser Glu Ala Glu Met Val Ser Ala Ile
         125                     130                     135

AAG CCT CGT GAA GAG TTC CTC AAC AGC CGG ATG CTG ATG CCC CAA        783
Lys Pro Arg Glu Glu Phe Leu Asn Ser Arg Met Leu Met Pro Gln
    140                     145                     150

GAC ATC ATG GCC TAT CGG GGT CGT GAG GTG GAG AAC CTG CCA            831
Asp Ile Met Ala Tyr Arg Gly Arg Glu Val Glu Asn Leu Pro
         155                     160                     165

CTG AGG AGC GCC CCT GGG TGT CGT GAG AGC AGA GCC TTT GCC CCC AGC CTG  879
Leu Arg Ser Ala Pro Gly Cys Arg Glu Ser Arg Ala Phe Ala Pro Ser Leu
    170                     175                     180

TAC AGT GGC CTG TCC ACA CCG GCC TCT TAT TCC ATG TAC AGC CAC        927
Tyr Ser Gly Leu Ser Thr Pro Ala Ser Tyr Ser Met Tyr Ser His
    185                     190                     195        200

CTC CCT GTC AGC AGC CTC TTC TCC GAT GAG GAG TTT CGG GAT GTC        975
Leu Pro Val Ser Ser Leu Phe Ser Asp Glu Glu Phe Arg Asp Val
    205                     210                     215

CGG ATG CCT GTG GCC AAC CCC TTC CCC AAG GAG CGG GCA CTC CCA TGT   1023
Arg Met Pro Val Ala Asn Pro Phe Pro Lys Glu Arg Ala Leu Pro Cys
    220                     225                     230
```

FIGURE 9C

```
GAT AGT GCC AGG CCA GTC CCT GGT GAG TAC AGC CGG CCG ACT TTG GAG    1071
Asp Ser Ala Arg Pro Val Pro Gly Glu Tyr Ser Arg Pro Thr Leu Glu
235                 240                 245

GTG TCC CCC AAT GTG TGC CAC AGC AAT ATC TAT TCA CCC AAG GAA ACA    1119
Val Ser Pro Asn Val Cys His Ser Asn Ile Tyr Ser Pro Lys Glu Thr
250                 255                 260

ATC CCA GAA GAG GCA CGA AGT GAT ATG CAC TAC AGT GTG GCT GAG GGC    1167
Ile Pro Glu Glu Ala Arg Ser Asp Met His Tyr Ser Val Ala Glu Gly
265                 270                 275                 280

CTC AAA CCT GCC GCC CCC TCA GCC CGA AAT GCC CCC TAC TTC CCT TGT    1215
Leu Lys Pro Ala Ala Pro Ser Ala Arg Asn Ala Pro Tyr Phe Pro Cys
285                 290                 295

GAC AAG GCC AGC AAA GAA GAG AGA CCC TCC TCG GAA GAT GAG ATT        1263
Asp Lys Ala Ser Lys Glu Glu Arg Pro Ser Ser Glu Asp Glu Ile
300                 305                 310

GCC CTG CAT TTC GAG CCC AAT GCA CCC CTG AAC CGG AAG GGT CTG        1311
Ala Leu His Phe Glu Pro Asn Ala Pro Leu Asn Arg Lys Gly Leu
315                 320                 325

GTT AGT CCA CAG AGC CCC AAA TCT GAC TGC CAG CCC AAC TCG CCC        1359
Val Ser Pro Gln Ser Pro Lys Ser Asp Cys Gln Pro Asn Ser Pro
330                 335                 340

ACA GAG GCC TGC AGT AAT AAG AAT ATC TGC GCC CTC CAG GGT TCT GGC    1407
Thr Glu Ala Cys Ser Asn Lys Asn Ile Cys Ala Leu Gln Gly Ser Gly
345                 350                 355                 360

TCC CCT CCA GCC AAG AGC CCC ACT GAC CCC AAA GCC TGC AGC TGG AAG    1455
Ser Pro Pro Ala Lys Ser Pro Thr Asp Pro Lys Ala Cys Ser Trp Lys
365                 370                 375
```

FIGURE 9D

```
AAA TAC AAG TTC ATC GTG CTC AAC AGC AAC CAG AAT GCC AAA CCA    1503
Lys Tyr Lys Phe Ile Val Leu Asn Ser Asn Gln Asn Ala Lys Pro
            380                 385                 390

GGG GGG CCT GAG CAG GCT GAG CTG GGC CGC CTT TCC CCA GCC TAC    1551
Gly Gly Pro Glu Gln Ala Glu Leu Gly Arg Leu Ser Pro Ala Tyr
            395                 400                 405

ACG GCC CCA CCT GCC TGC CAG CCC ATG GAG CCT GAG AAC CTT GAC    1599
Thr Ala Pro Pro Ala Cys Gln Pro Met Glu Pro Glu Asn Leu Asp
            410                 415                 420

CTC CAG TCC CCA ACC AAG CTG AGT GCC AGC GGG GAG GAC TCC ACC ATC    1647
Leu Gln Ser Pro Thr Lys Leu Ser Ala Ser Gly Glu Asp Ser Thr Ile
            425                 430                 435                 440

CCA CAA GCC AGC CGG CTC AAT ATC GTT AAC ATC TCA CCA CTC TAC ATG CAC CCC    1695
Pro Gln Ala Ser Arg Leu Asn Ile Val Asn Ile Ser His Pro Leu Tyr Met Gly
            445                 450                 455

TCT CCC CGC AGC AGC GAG AGC AGC CAC ATC GTT AAC ATC TCA CCA CTC TAC ATG CAC CCC    1743
Ser Pro Arg Ser Ser Glu Ser Ser His Pro Leu Tyr Met Gly
            460                 465                 470

CCG AAG TGC ACG TCC TGC GGC TCT CAG TCC CCA CAG TCC CCA CAT GCA GAG ATG    1791
Pro Lys Cys Thr Ser Cys Gly Ser Gln Ser Pro Gln Ser Pro Gln His Ala Glu Met
            475                 480                 485

TGC CTC CAC ACC GCT GGC CCC ACG TTC GCT GAG ATG GGA GAG ACC    1839
Cys Leu His Thr Ala Gly Pro Thr Phe Ala Glu Met Gly Glu Thr
            490                 495                 500

CAG TCT GAG TAC TCA GAT TCT AGC TGT GAG AAC GGG GCC TTC TGC    1887
Gln Ser Glu Tyr Ser Asp Ser Ser Cys Glu Asn Gly Ala Phe Cys
            505                 510                 515                 520
```

FIGURE 9E

```
AAT GAG TGT GAC TGC CGC TTC TCT GAG GAG GCC TCA CTC AAG AGG CAC    1935
Asn Glu Cys Asp Cys Arg Phe Ser Glu Glu Ala Ser Leu Lys Arg His
                525                 530                 535

ACG CTG CAG ACC CAC AGT GAC AAA CCC TAC AAG TGT GAC CGC TGC CAG    1983
Thr Leu Gln Thr His Ser Asp Lys Pro Tyr Lys Cys Asp Arg Cys Gln
            540                 545                 550

GCC TCC TTC CGC TAC AAG GGC AAC CTC GCC AGC CAC AAG ACC GTC CAT    2031
Ala Ser Phe Arg Tyr Lys Gly Asn Leu Ala Ser His Lys Thr Val His
        555                 560                 565

ACC GGT GAG AAA CCC TAT CGT TGC AAC ATC TGT GGG GCC CAG TTC AAC    2079
Thr Gly Glu Lys Pro Tyr Arg Cys Asn Ile Cys Gly Ala Gln Phe Asn
    570                 575                 580

CGG CCA GCC AAC CTG AAA CTG AAA ACC CAC ACT CGA ATT CAC TCT GGA GAG AAG    2127
Arg Pro Ala Asn Leu Lys Thr His Thr Arg Ile His Ser Gly Glu Lys
585                 590                 595                 600

CCC TAC AAA TGC GAA ACC TGC GGA GCC AGA TTT GTA CAG GTG GCC CAC    2175
Pro Tyr Lys Cys Glu Thr Cys Gly Ala Arg Phe Val Gln Val Ala His
                605                 610                 615

CTC CGT GCC CAT GTG CTT ATC CAC CTT CAG CAC ACT CTG AAG AGC CAC    2223
Leu Arg Ala His Val Leu Ile His Leu Gln Thr Leu Lys Ser His
            620                 625                 630

GAA ATC TGT GGC ACC CGT TTC CGG AGG GAG AAA CCT TAC CAT TGT GAG AAG TGT AAC    2271
Glu Ile Cys Gly Thr Arg Phe Arg Arg Glu Lys Pro Tyr His Cys Glu Lys Cys Asn
        635                 640                 645

CTG CGA ATC CAC ACA GGA GAG ATC CAC ACA GGA ATC CAC ACA GGA GAG AAA CCT TAC CAT TGT GAG AAG TGT AAC    2319
Leu Arg Ile His Thr Gly Glu Ile His Thr Gly Glu Lys Pro Tyr His Cys Glu Lys Cys Asn
    650                 655                 660
```

FIGURE 9F

```
CTG CAT TTC CGT CAC AAA AGC CAG CTG CGA CTT CAC TTG CGC CAG AAG    2367
Leu His Phe Arg His Lys Ser Gln Leu Arg Leu His Leu Arg Gln Lys
665                     670                 675                 680

CAT GGC GCC ATC ACC AAC ACC AAG GTG CAA TAC CGC GTG TCA GCC ACT    2415
His Gly Ala Ile Thr Asn Thr Lys Val Gln Tyr Arg Val Ser Ala Thr
            685                 690                 695

GAC CTG CCT CCG GAG CTC CCC AAA GCC TGC TGAAGCATGG AGTGTTGATG      2465
Asp Leu Pro Pro Glu Leu Pro Lys Ala Cys
                700                 705

CTTTCGTCTC CAGCCCCTTC TCAGAATCTA CCCAAAGGAT ACTGTAACAC TTTACAATGT  2525

TCATCCCATG ATGTAGTGCC TCTTTCATCC ACTAGTGCAA ATCATAGCTG GGGGTTGGGG  2585

GTGGTGGGG TCGGGCCTG GGGGACTGGG AGCCGCAGCA GCTCCCCCTC CCCCACTGCC    2645

ATAAAACATT AAGAAAATCA TATTGCTTCT TCTCCTATGT GNNNNNNNNN NNNNNNNNNN  2705

NNNNNNNNNN NNNNNNNNNN NNNNNNNNNN NNNNNNNNNN NNNNNNNNNN NNNNNNNNNN  2765

NNNNNNNNNN NNNNNNNNNN NNNNNNNNNN NNNNNNNNNN NNNNNNNNNN NNNNNNNNNN  2825

NNNNNNNNNN NNNNNNNNNN NNNNNNNNNN NNNNNNNNNN NNNNNNNNNN NNNNNNNNNN  2885

NNNNNNNNNN NNNNNNNNNN NNNNNNNNNN NNNNNNNNNN NNNNNNNNNN NNNNNNNNNN  2945

NNNNNNNNNN NNNNNNNNNN NNNNNNNNNN NNNNNNNNNN NNNNNNNNNN NNNNNNNNNN  3005

NNNNNNNNNN NNNNNNNNNN NNNNNNNNNN NNNNNNNNNN NNNNNNNNNN NNNNNNNNNN  3065

NNNNNNNNNN NNNNNNNNNN NNNNNNNNNN NNNNNNNNNN NNNNNNNNNN NNNNNNNNNN  3125
```

FIGURE 9G

```
NNNNNNNNNN NNNNNNNNNN NNNNNNNNNN NNNNNNNNNN NNNNNNNNNN NNNNNNNNNN  3185
NNNNNNNNNN NNNNNNNNNN NNNNNNNNNN NNNNNNNNNN NNNNNNNNNN NNNNNNNNNN  3245
NTTTAAGTAT TGCATCTGTA TAAGTAAGAA AATATTTTGT CTAAAATGCC TCAGTGTATT  3305
TGTATTTTTT TGCAAGTGGG GGGTTACAAT TTACCCAGTG TGTATTAAAA AAAACCCAAA  3365
GAACCCAAAA ATCTCCAGAA GGAAAAATGT GTAATTTTGT TCTAGTTTTC AGTTGTATA   3425
TACCCGTACA ACGGTGCCTC TTTTCACGGA AGTTTTCAAT GATGGGCGAG             3485
CGTGCACCAT CCCTTTTTGA AGTGTAGGCA GACACAGGGA CTTGAAGTTG TTACTAACTA  3545
AACTCTCTTT GGGAATGTTT GTCTCATCCC ANTCTGCGTC ATGCTGTGT GATAACTACT   3605
CCGGAGACAG GGTTTGGCTG TGTCTAAACT GCATTACCGC GTTGTAAAAA ATAGCTGTAC  3665
CAATATAAGA ATAAAATGTT GGAAAGTCGC AAAAAAAAAA AAAAAAAAAA AAAAA       3720
```

CLONING AND USES OF THE GENETIC LOCUS BCL-6

The invention disclosed herein was made with Government support under NIH Grant No. CA-44029, CA-34775 and CA-08748 from the Department of Health and Human Services. Accordingly, the U.S. Government has certain rights in this invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Non-random chromosomal abnormalities are found in up to 90% of patients with non-Hodgkin's lymphoma (NHL) and have been shown to play an important role in lymphomagenesis by activating proto-oncogenes (1). Some of these translocations, which are associated with specific histologic subsets of NHL, have been characterized at the molecular level. In the t(8;14), t(8;22), and t(2;8) translocations associated with Burkitt Lymphoma, L₃-type acute lymphoblastic leukemia and AIDS-associated non-Hodgkin lymphoma (NHL), a known proto-oncogene, c-myc, was found juxtaposed to the immunoglobulin (Ig) loci (2,3). In the t(14;18) translocation, which is implicated in follicular-type NHL, molecular analysis of the sequences linked to the Ig locus led to the identification of a novel proto-oncogene, bcl-2 (4–6). The t(11;14)(q13;q32), mainly associated with "mantle zone" lymphoma, appears to involve the juxtaposition of the Ig heavy-chain locus with the bc1-1 locus, the site of the candidate proto-oncogene PRAD-1/cyclin D1 (7,8). These well characterized chromosome translocations are associated, however, with only a fraction of NHL cases, while a number of other recurrent translocations remain to be characterized for their genetic components.

One important example of such cytogenetic abnormalities is represented by various alterations affecting band 3q27. This region is involved in translocations with various chromosomal sites including, but not limited, to those carrying the Ig heavy-(14q32) or light-(2p12, 22q11) chain loci (9,10). Overall, 3q27 breakpoints are detectable in 7–12% of B-cell NHL cases by cytogenetic analysis, with t(3;22) (q27;q11) being the most frequent type detectable in 4–5% of NHL (9). The clinicopathologic relevance of 3q27 breakpoints is underscored by its consistent association with diffuse-type NHL, a frequent and clinical aggressive subtype for which no specific molecular lesion has yet been identified (9).

The recurrence of 3q27 breakpoints in NHL has prompted a search for the corresponding proto-oncogene. This invention discloses the cloning of clustered 3q27 breakpoints from two NHL cases carrying t(3;14)(q27;q32) translocations and the identification of genomic rearrangements within the same breakpoint region in additional NHL cases carrying translocations involving 3q27. Within the same region, a transcriptional unit has been identified, which represents the candidate proto-oncogene (bcl-6) associated with 3q27 translocations in B-NHL.

SUMMARY OF THE INVENTION

This invention provides an isolated vertebrate nucleic acid molecule of bcl-6 locus. This invention provides an isolated vertebrate DNA molecule of bcl-6 locus. This invention provides an isolated vertebrate cDNA molecule of bcl-6. This invention provides an isolated genomic DNA molecule of bcl-6. This invention provides an isolated vertebrate RNA molecule of bcl-6. This invention provides an isolated human nucleic acid molecule of bcl-6 locus.

This invention provides a nucleic acid molecule comprising a nucleic acid molecule of at least 15 nucleotides capable of specifically hybridizing with a sequence included within the sequence of the nucleic acid molecule of bcl-6.

This invention provides an isolated vertebrate DNA molecule of bcl-6 operatively linked to a promoter of RNA transcription. This invention provides a vector which comprises the isolated vertebrate DNA molecule of bcl-6.

This invention provides the above vector, wherein the isolated nucleic acid molecule is linked to a plasmid.

This invention provides a host vector system for the production of a polypeptide encoded by bcl-6 locus, which comprises the above vector in a suitable host.

This invention provides a method of producing a polypeptide encoded by bcl-6 locus, which comprises growing the above host vector system under suitable conditions permitting production of the polypeptide and recovering the polypeptide so produced.

This invention provides a polypeptide encoded by the isolated vertebrate nucleic acid molecule of bcl-6 locus. This invention provides an antibody capable of binding to polypeptide encoded by bcl-6 locus.

Finally, this invention provides a method for diagnosing B-cell lymphoma in a subject.

BRIEF DESCRIPTION OF THE FIGURES

FIG. 2. Molecular cloning of the chromosomal breakpoints from two NHL cases with t(3;14). Illustrated are the maps of two representative phage clones spanning the breakpoint regions in case SM1444 (SM-71) and KC1445 (KC-51). Chromosome 14 portions of the phage inserts are indicated by a solid line with hatched and black boxes representing switch sequences and $C_\mu$ exons, respectively. Vertical arrows point to the junctions of chromosome 3 and 14 sequences. The probes used for Southern (FIGS. 4A, 4B and 4C) and Northern (FIG. 5) analysis are illustrated below the SM-71 map. Restriction enzyme sites are indicated as: B=BamHI; H=HindIII; R=EcoRI; G=BblII; S=sacI.

FIG. 5. Identification of the bcl-6 transcriptional unit. 15 μg of total RNA isolated from the indicated human cell lines was analyzed by Northern blot hybridization using the Sac 4.0 probe (see FIG. 2). CB33:EBV-immortalized human B lymphoblastoid cell line; HeLa: human cervical carcinoma cell line; Daudi: human Burkitt lymphoma cell line; Hut78: human T-cell leukemia cell line. Hybridization of the same filter to a mouse GAPDH probe is shown as control for RNA amount loaded in each lane. The faint band comigrating with 28S RNA in all the lanes may be the result of cross-hybridization with ribosomal RNA sequences.

FIGS. 9A, 9B, 9C, 9D, 9E, 9F and 9G. CDNA and Amino Acid Sequences of BCL-6 (SEQ ID NOs. 1 and 2). The Sac 4.0 probe was used to screen a recombinant phage cDNA library constructed from Bjab B cell lymphoma line RNA. A 4.0 kilobase cDNA was isolated and its nucleotide sequence was determined (20). It contains a long open reading frame potentially coding for 706 amino acid protein which contains five zinc-finger domains (underlined in the figure; C and H residues which identify the C2H2-type zinc-finger structure are indicated in bold).

DETAILED DESCRIPTION OF THE INVENTION

Figure 1:
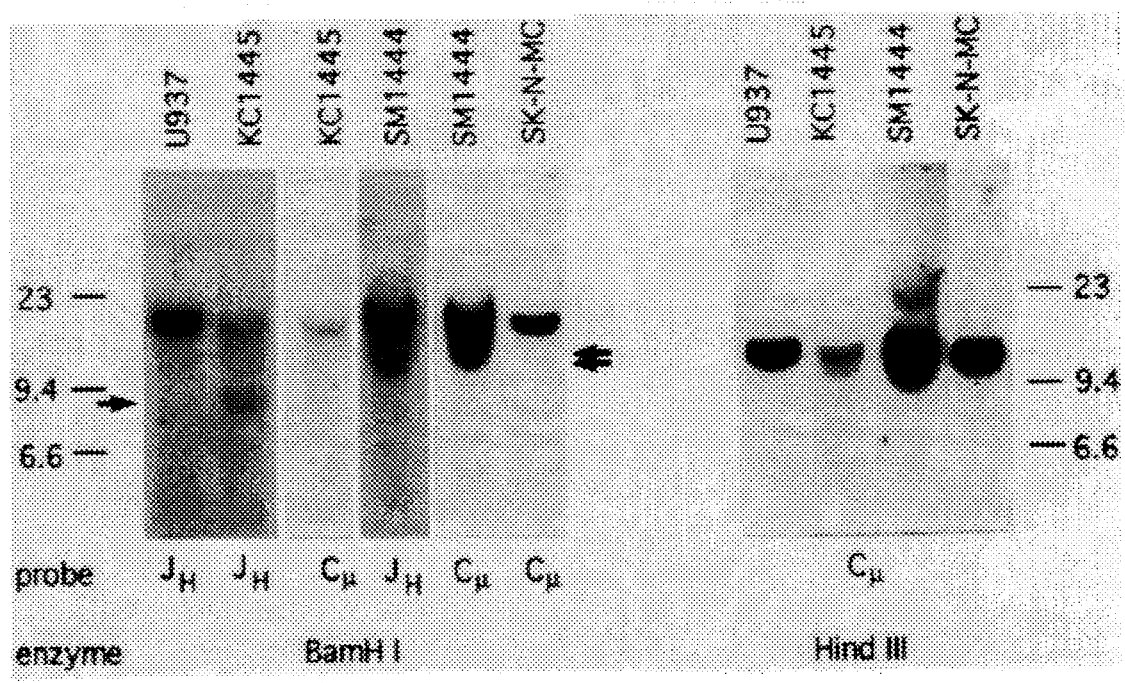
FIG. 1. Immunoglobulin gene rearrangement analysis of KC1445 and SM1444 DNA. DNA extracted from the cell lines U937 (monocytic leukemia) and SK-N-MC (neuroblastoma) were used as controls for non-rearranged, germ-line Ig genes. In the left panel, the arrow on the left points to the rearranged $J_H$ fragment which does not contain $C_\mu$ sequences in KC1445 DNA, while the two arrows on the right point to the two distinct fragments containing $J_H$ or $C_\mu$ sequences in SM1444 DNA.

The following standard abbreviations are used throughout the specification to indicate specific nucleotides:

| C = cytosine | A = adenosine |
|---|---|
| T = thymidine | G = guanosine |

This invention provides an isolated vertebrate nucleic acid molecule of the bcl-6 locus. As used herein, bcl-6 locus means the breakpoint cluster region in B-cell lymphomas. The bcl-6 locus is of 30 kilobase in length containing at least a bcl-6 gene which codes for a protein. Therefore, the bcl-6 locus contains both the 5' and 3' flanking region of the coding sequences of the bcl-6 gene.

In an embodiment, the isolated, vertebrate nucleic acid molecule of bcl-6 locus is DNA. In another embodiment, the isolated, vertebrate nucleic acid of the bcl-6 locus is cDNA. In a further embodiment, the isolated, vertebrate nucleic acid is genomic DNA. In a still further embodiment, the isolated, vertebrate nucleic acid molecule is RNA.

This invention provides an isolated, human nucleic acid molecule comprising the bcl-6 locus.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated vertebrate nucleic acid molecules are useful for the development of probes to study B cell lymphomas.

This invention provides a nucleic acid molecule comprising a nucleic acid molecule of at least 15 nucleotides capable of specifically hybridizing with a sequence included within the sequence of the bcl-6 locus. In an embodiment, this molecule is DNA. In another embodiment, the molecule is RNA.

As used herein, the phrase "specifically hybridizing" means the ability of a nucleic acid molecule to recognize a nucleic acid sequence complementary to its own and to form double-helical segments through hydrogen bonding between complementary base pairs.

The above nucleic acid molecule of at least 15 nucleotides capable of specifically hybridizing with a sequence of bcl-6 locus may be used as a probe for bcl-6 sequences. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the bcl-6 locus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the bcl-6 locus downstream of a bacteriophage promoter such as T3, T7 or SP6. Large amounts of RNA probe may be produced by incubating the labeled nucleotides with a linearized bcl-6 or its fragment where it contains an upstream promoter in the presence of the appropriate RNA polymerase.

This invention provides an cDNA molecule of bcl-6 locus operatively linked to a promoter of RNA transcription.

This invention provides a vector which comprises the nucleic acid molecule of bcl-6 locus. This invention provides the above vector, wherein the isolated nucleic acid molecule is linked to a plasmid.

This invention further provides isolated cDNA molecule of the bcl-6 locus operatively linked to a promoter of RNA transcription. Various vectors including plasmid vectors, cosmid vectors, bacteriophage vectors and other viruses are well known to ordinary skilled practitioners.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Figure 8:
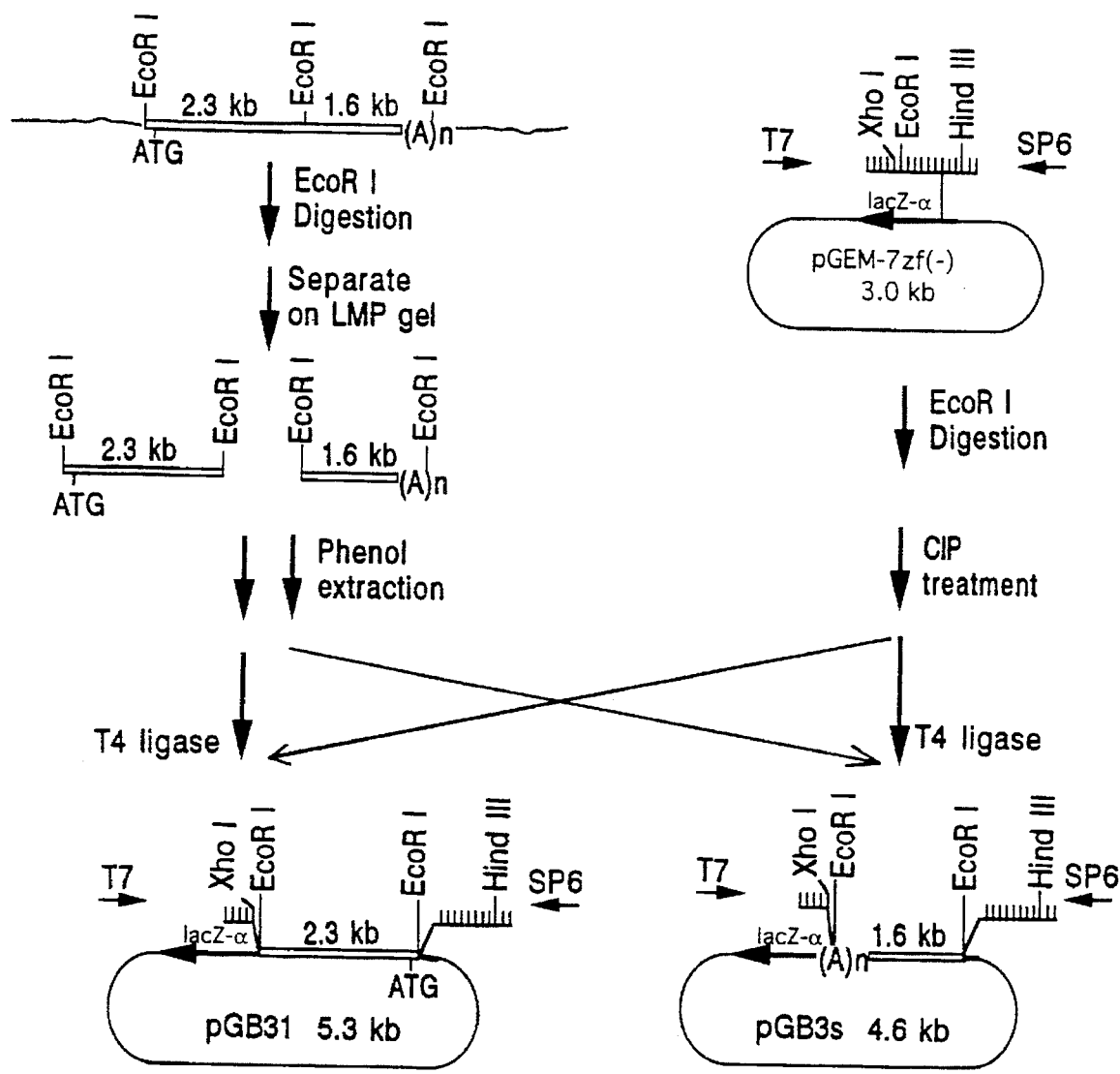
FIG. 8. pGB31 and pGB3s plasmid construction.

In an embodiment, a partial cDNA molecule of the bcl-6 locus is linked to pGEM-7zf(−) and the resulting plasmid is designated as pGB31 (FIG. 8). Plasmid, pGB31 was deposited on Jun. 3, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pGB31 was accorded with ATCC Accession Number 75476.

In an another embodiment, a partial cDNA molecule of the bcl-6 locus is linked to pGEM-7zf(−) and the resulting plasmid is designated as pGB3s (FIG. 8). Plasmid, pGB3s was deposited on Jun. 3, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pGB3s was accorded with ATCC Accession Number 75477.

This invention provides a host vector system for the production of a polypeptide encoded by bcl-6 locus, which comprises the above vector in a suitable host.

This invention provides the above host vector system, wherein the suitable host is a bacterial cell, insect cell, or animal cell.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general. Expression vectors are useful to produce cells that express the polypeptide encoded by the bcl-6 locus.

This invention further provides an isolated DNA or cDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention provides a method of producing a polypeptide encoded by bcl-6 locus, which comprises growing the above host vector system under suitable conditions permitting production of the polypeptide and recovering the polypeptide so produced.

This invention provides a polypeptide encoded by the isolated vertebrate nucleic acid molecule of bcl-6 locus.

This invention provides an antibody capable of binding to polypeptide encoded by bcl-6 locus. In an embodiment, the antibody is monoclonal.

This invention provides a method to select specific regions on the polypeptide encoded by the bcl-6 locus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the bcl-6 locus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the bcl-6 locus in living animals, in humans, or in biological tissues or fluids isolated from animals or humans.

This invention provides a method of diagnosing diffuse-type B-cell lymphoma in a subject which comprises detecting in a sample from the subject nucleic acid molecule of bcl-6 locus.

This invention provides a method for diagnosing B-cell lymphoma in a subject comprising: (a) obtaining DNA sample from the subject; (b) cleave the DNA sample into fragments; (c) separating the DNA fragments by size fractionation; (d) hybridizing the DNA fragments with a nucleic acid molecule comprising a nucleic acid molecule of at least 15 nucleotides capable of specifically hybridizing with a sequence included within the sequence of the nucleic acid molecule of the bcl-6 locus to detect the DNA fragment containing the bcl-6 sequence; and (e) comparing the detected DNA fragment from step (d) with the DNA fragment from a known normal subject, the difference in size of the fragments indicating the occurrence of B-cell lymphoma in the subject. In a preferred embodiment, the above diagnostic method is for diffuse-type B-cell lymphomas.

A person of ordinary skill in the art will be able to obtain appropriate DNA sample for diagnosing B-cell lymphoma in a subject. The DNA sample obtained by the above described method may be cleaved by restriction enzyme. The uses of restriction enzymes to cleave DNA and the conditions to perform such cleavage are well-known in the art.

In an embodiment, the size fractionation in step (c) of the above-described method is effected by a polyacrylamide gel. In another embodiment, the size fractionation is effected by an agarose gel.

This invention also provides the above-described diagnosis method wherein step the nucleic acid molecule in step (d) is labeled with a detectable marker. The detectable marker includes but is not limited to a radiolabelled molecule, a fluorescent molecule, an enzyme, or a ligand.

In a preferred embodiment, the above-described diagnosis method further comprises transferring the DNA fragments into a solid matrix before the hybridization step (d). One example of such solid matrix is nitrocellulose paper.

Figure 4A:
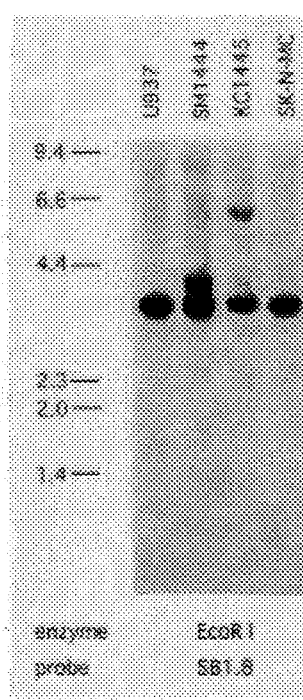
FIGS. 4A, 4B and 4C. Southern blot hybridization analysis of bcl-6 rearrangements in NHL carrying 3q27 breakpoints. The probes used are illustrated in FIG. 2. U937 and SK-N-MC DNAs are used as germ-line controls since their hybridization pattern was identical to the one observed in a panel of 19 control DNAs tested. The detected cytogenetic abnormalities affecting 3q27 in each case are: KC1445: t(3;14) (q27;q32); SM1444: t(3;14) (q27;q32); TF1403: t(3;14) (q27;q32); LD1411: t(3,14) (q27;q32); EM352: t(3;22) (q27;q11); CF755: t(3;12) (q27;q11); SO955:der(3) t(3;5) (q27;q31).
Figure 4B:
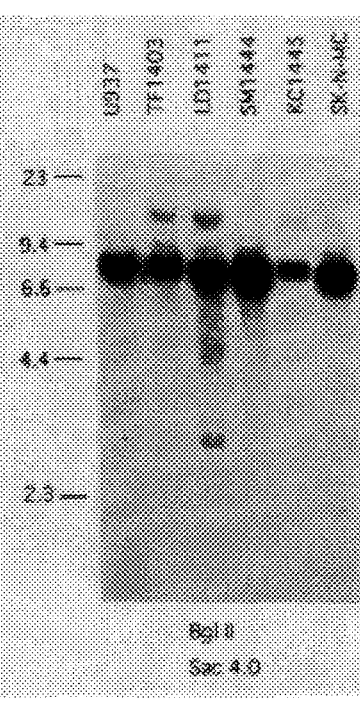
Figure 4C:
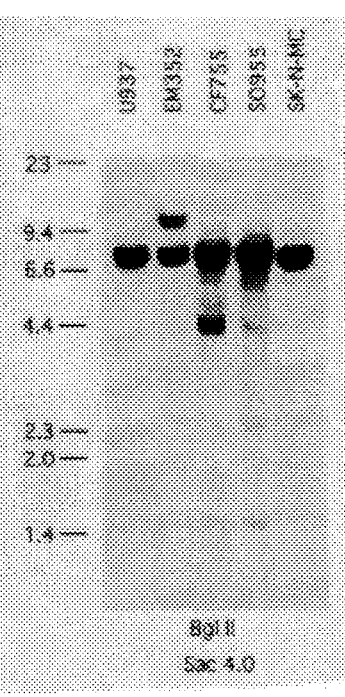
Figure 6:
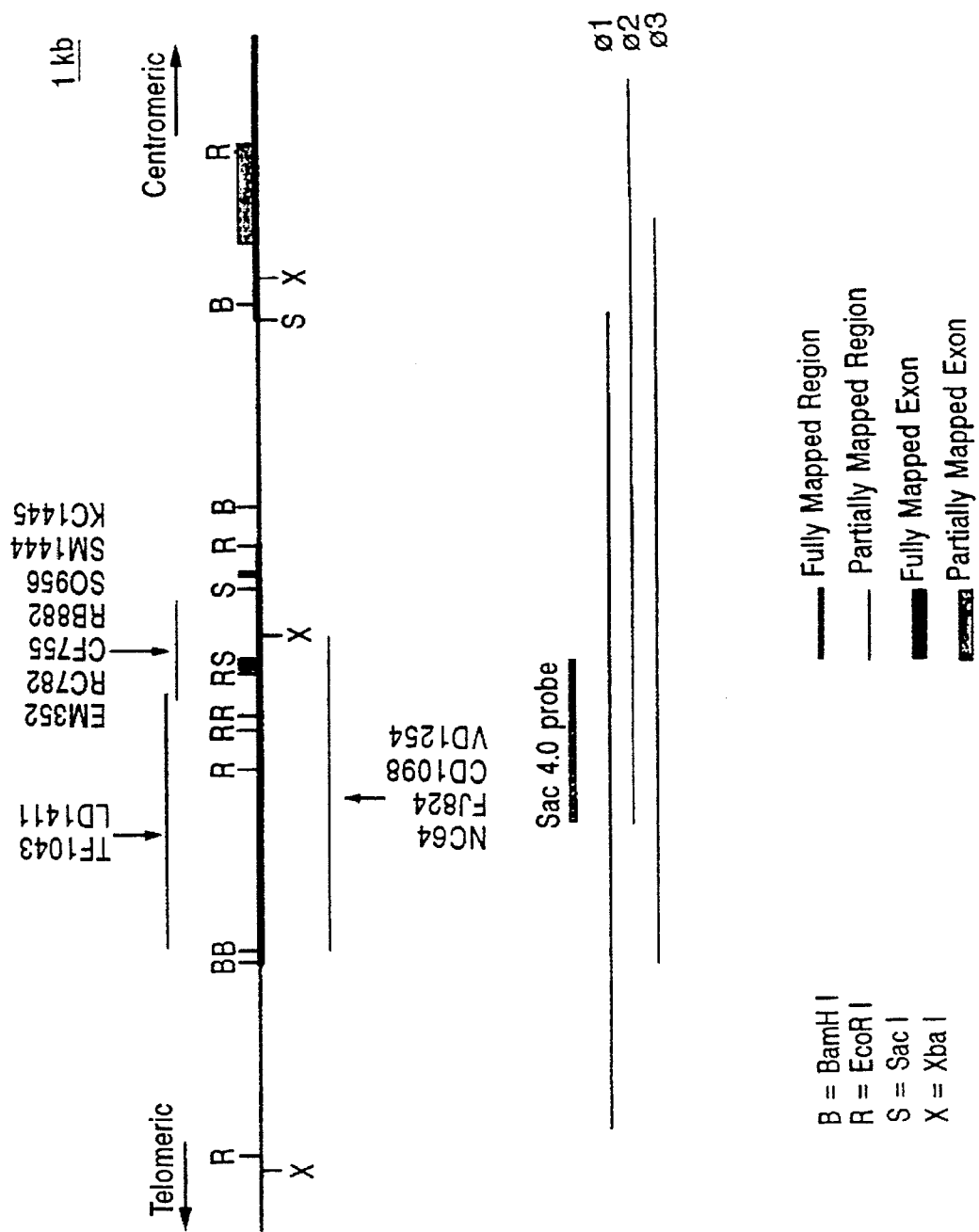
FIG. 6. Map of normal human BCL-6 locus. A recombinant genomic DNA library derived from normal placenta DNA was obtained from STRATAGENE Inc and screened by plaque hybridization using the Sac 4.0 probe. Three recombinant phages were obtained (φ 1–3 in the figure) whose inserts have been mapped and shown to overlap on approximately 30 kilobases of genomic DNA representing the BCL-6 locus. These sequences containing bcl-6 exons since they hybridize to the cDNA probe. The precise position of the exons has only been approximately determined and is schematically indicated in the figure. The position of the breakpoints observed in various lymphoma cases is also indicated.
Figure 7:
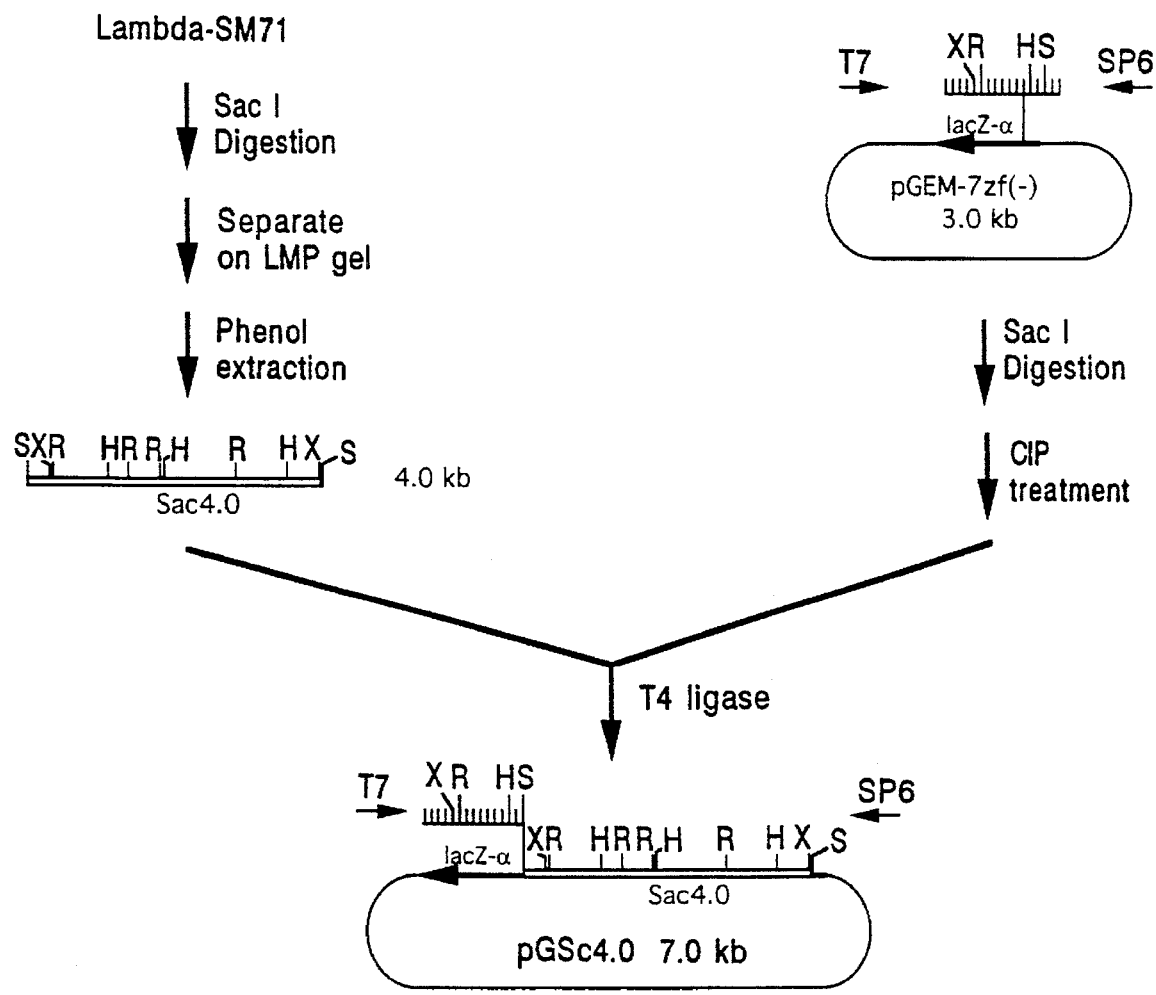
FIG. 7. pSac 40 plasmid construction.

As an example for the above-described diagnosis method is shown in FIGS. 4A, 4B and 4C where different NHL sample are analyzed. More lymphoma cases and their breakpoints are shown in FIG. 6.

This invention also provides a method for diagnosing B-cell lymphoma in a subject comprising: (a) obtaining RNA sample from the subject; (b) separating the RNA sample into different species by size fractionation; (c) hybridizing the RNA species with a nucleic acid molecule comprising a nucleic acid molecule of at least 15 nucleotides capable of specifically hybridizing with a sequence included within the sequence of the nucleic acid molecule of the bcl-6 locus to detect the RNA species containing the bcl-6 sequence; and (d) comparing the RNA species obtained from (c) with the RNA species from a known normal subject, the difference it, size of the species indicating the occurrence of B-cell lymphoma in the subject.

In an embodiment, the size fractionation in step (b) is effected by a polyacrylamide or agarose gel.

This invention also provides the above-described method where in step (c), the nucleic acid molecule is labeled with a detectable marker. The detectable marker includes but is not limited to a radiolabelled molecule, a fluorescent molecule, an enzyme, or a ligand.

This invention also provides the above-method further comprises transferring the RNA species into a solid matrix before step (c).

This invention also provides various uses of bcl-6 locus/gene an its derivatives. This invention further provides a method for diagnosis of B cell lymphoma and/or diffuse-type B cell lymphoma using bcl-6 DNA probes or synthetic oligonucleotide primers derived from bcl-6 sequences to detect bcl-6 rearrangements/mutations by Southern blotting PCR or other DNA based techniques.

This invention also provides a method of diagnosis of B cell lymphoma and/or diffuse-type B cell lymphoma using bcl-6 DNA probes or synthetic oligonucleotide primers derived from bcl-6 sequences to detect abnormal bcl-6RNA species by Northern blotting, PCR or other RNA-based techniques.

This invention further provides a method of diagnosis of B cell lymphoma and/or diffuse-type B cell lymphoma using antiserum or monoclonal antibodies directed against the bcl-6 protein product(s).

Finally, this invention provides a therapy of B cell lymphoma and/or diffuse-type B cell lymphoma using anti bcl-6 reagents including specific antisense sequences and compounds interfering with bcl-6 functions.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

DNA Extraction and Southern Blot Analysis. Total genomic DNA was purified from frozen tumor biopsies by cell lysis, proteinase K digestion, "salting-out" purification and ethanol precipitation as previously described (11). Southern blot hybridization analysis was performed in 50% formamide, 3X SSC, 10X dextran sulphate, 5X Denhardt's solution, 0.5% SDS at 37° C. for 16 hrs. Filters were washed in 0.2X SSC, 0.5% SDS at 60° C. for 2 hrs. DNA probes were $^{32}$P-labelled by the random priming method (12).

DNA Probes. The following probes were used for Southern blot analysis of Ig gene rearrangements: i) ($J_H$) probe: 6.6 kb BamHi/HindIII fragment from the human Ig heavy-chain ($Ig_H$) locus (13); ii) ($C_\mu$) probe: 1.3 kb EcoRI fragment containing the first two exons of human $C_\mu$ (13).

Genomic Cloning. Genomic libraries from NHL cases SM1444 and KC1445 were constructed by partial Sau 3A restriction digestion of genomic DNA and ligation of gel-purified 15–20 kb fractions into LambdaGem-11 phage vector (Promega). Library screening was performed by plaque-hybridization using the $C_\mu$ probe.

Fluorescence in situ Hybridization Analysis (FISH). Phage DNA was labelled with biotin-14-dATP by nick translation and hybridized to metaphase spreads from normal human lymphocytes as described (14). To visualize the hybridization signal and the corresponding bands sequentially under the microscope, the slides were stained and counterstained with propidium iodide and 4'6"-diamideno-2-phenylindole (DAPI), respectively.

Northern Blot Hybridization Analysis. RNAs from several human cell lines were extracted by the guanidine-isothiocyanate method (15). For Northern blot analysis, RNA samples were electrophoresed through 0.9% agarose-2.2M formaldehyde gels and then transferred to nitrocellulose filters. Hybridization and washing were performed as described for Southern blot analysis.

Experimental Results

DNA was extracted from tumor tissue of two cases (SM1444 and KC1445) of IgM-producing, diffuse-type B-cell NHL carrying the t(3;14)(q27;q32) translocation. Since the involvement of the $Ig_H$ locus was suspected based on the 14q32 breakpoint, SM1444 and KC1445 DNAs were first analyzed by Southern blot hybridization using combinations of enzymes and probes specific for the $J_H$ and $C_\mu$ regions of the $Ig_H$ locus (13). In both cases, digestion by BamHI showed rearranged fragments containing $J_H$ sequences (FIG. 1). Subsequent hybridizations to the $C_\mu$ probe showed, in each case, that one rearranged fragment containing $J_H$ sequences was not linked to $C_\mu$ sequences (see failure of the $C_\mu$ probe to hybridize to the same rearranged BamHI fragment detected by $J_H$; FIG. 1) as would be expected for the physiologically rearranged $Ig_H$ allele in IgM producing cells. In addition, in both cases, digestion with HindIII and hybridization with $C_\mu$ detected a rearranged fragment, a finding inconsistent with either germ-line or physiologically rearranged $Ig_H$ genes, since both HindIII sites flanking $C_\mu$ sequences are not involved in V-D-J arrangements (13). The observed pattern is, however, consistent with chromosomal breakpoints located within $C_\mu$ switch sequences, as previously observed in several cases of chromosomal translocations involving the $Ig_H$ locus (2,16–18).

Based on this analysis, the $C_\mu$ containing fragments from each case were cloned by screening genomic libraries constructed from SM1444 and KC1445 DNAs using the $C_\mu$ probe. Restriction mapping and hybridization analysis of several phage clones led to the identification of recombinant phages from each library which contained $C_\mu$ sequences linked to sequences unrelated to the $Ig_H$ locus (see FIG. 2 for maps of representative phage clones). The Ig portions of the phage inserts overlapped along the $C_\mu$ region extending 5' into the switch region where alignment with the restriction map of the normal Ig heavy-chain locus was lost. The location of the breakpoint within $C_\mu$ switch sequences was confirmed for case SM1444 by DNA sequence analysis of the breakpoint junction of phage SM-71 (data not shown), which revealed the presence of the repeated motifs typical of the $Ig_H$ switch regions on the chromosome 14 side (19). The Ig-unrelated portions of phage SM-71 and KC-51 also overlapped with each other in their restriction maps, suggesting that they were derived from the same genomic region. This notion is further supported by the fact that probe Sac 4.0 derived from SM-71 was able to hybridize to the corresponding region of KC-51 in Southern blot analysis (not shown).

Figures 3A, 3B:
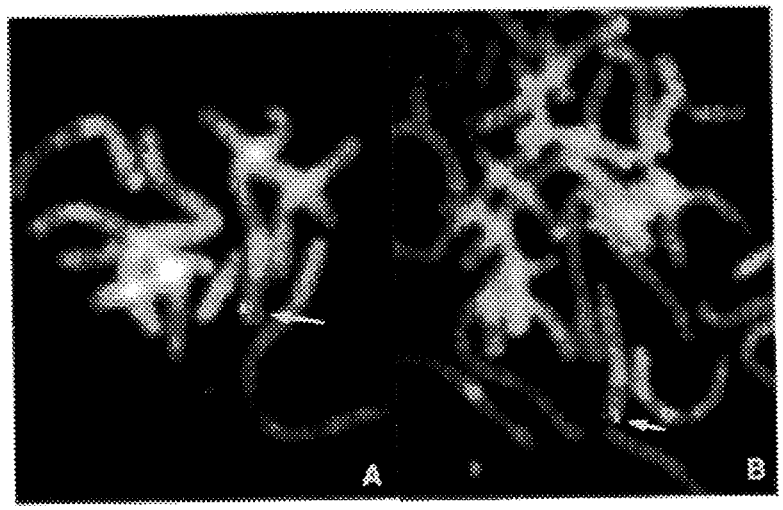
FIGS. 3A and 3B. 3A. Localization of phage SM-71 sequences to chromosome 3 by fluorescence in situ hybridization. 3B. Localization of phage SM-71 sequences to chromosome 14 by fluorescence in situ hybridization. Consistent hybridization signals at 3q27 (arrow in panel A) and 14q32 (arrow in panel B) demonstrated that the insert is derived from the translocation junction.

To determine the chromosomal origin of the Ig-unrelated sequences, a recombinant phage (SM-71) derived from case SM1444, was used as a probe in FISH analysis on metaphase chromosome spreads from mitogen-stimulated normal blood lymphocytes. The phage probe hybridized specifically to chromosome 14q32 as well as to chromosome 3q27 (FIGS. 3A and 3B), indicating that the recombinant phage insert contained one of the two chromosomal junctions of the reciprocal t(3;14) translocation. Thus, taken together, the results of cloning and FISH analysis established that, in both NHL cases studied, the chromosomal translocation has linked sequences within the switch region of the $C_\mu$ locus to sequences from band 3q27, consistent with the cytogenetic description of the t(3;14)(q27;q32) translocation. In the two NHL cases studied, the breakpoints on 3q27 were located within 3 kb of the same genomic locus, which was termed bcl-6.

In order to determine whether 3q27 breakpoints in additional NHL cases were also located within the cloned portion of the bcl-6 locus, bcl-6 rearrangements were examined in a total of 19 NHL cases carrying 3q27 breakpoints, including 4 (two cloned cases and two additional ones) carrying t(3;14)(q27;q32) as well as 15 cases carrying 3q27 translocations involving regions other than 14q32. Southern blot hybridization using probes derived from phage SM-71 (see FIG. 2) detected rearranged fragments in EcoRI-and/or BglII-digested DNA in 7 of 19 cases studied, including all 4 t(3;14) cases as well as 3 cases with other types of translocations (see FIGS. 4A, 4B and 4C for cytogenetic description of the cases and representative results). These results indicate that heterogeneous 3q27 breakpoints cluster in a fairly restricted region within bcl-6 independently of the partner chromosome involved in the translocation.

Whether the bcl-6 locus adjacent to the chromosomal breakpoints contained a transcriptional unit was investigated. Probe Sac 4.0 (see FIG. 2) was used to detect RNA expression in several human cell lines by Northern blot analysis. A major 2.4 kb RNA species was readily detectable in two B-cell derived cell lines tested, while a relatively less abundant 4.4 kb species is present in CB33 only. No hybridization was detected in a T-cell derived cell line (HUT 78) nor in HeLa cells (FIG. 5). This result indicates that 3q27 sequences immediately adjacent to the chromosomal breakpoint cluster are part of a gene (bcl-6) which is expressed in cells of the B lineage.

Experimental Discussion

This study reports the identification and cloning of a genomic region, bcl-6, involved in recurrent chromosomal translocations affecting band 3q27 in NHL. The region is defined by the clustered position of breakpoints in seven NHL cases carrying 3q27 translocations involving either IgH or several other loci. A more precise definition of the bcl-6 locus and of the frequency of its involvement in NHL requires cloning and characterization of additional bcl-6 sequences and studying additional tumor cases. Nevertheless, the finding that various translocation partner chromosomes have been joined to the same region on chromosome 3 in cytogenetically heterogenous NHL cases supports the notion that rearrangement of the bcl-6 locus may represent the critical common denominator of translocations involving 3q27.

The second finding of this study is that the bcl-6 locus contains a gene which is expressed in B-cells. It is not clear at this stage whether the chromosomal breakpoints directly truncate coding or regulatory sequences of bcl-6, or, whether the gene remains intact with its regulation overridden by transcriptional control motifs juxtaposed by the translocation. The clustering of breakpoints in the seven studied NHL cases suggests, however, that bcl-6 may be a proto-oncogene which can contribute to NHL pathogenesis upon activation by chromosomal translocation. Results of this study will allow elucidation of the normal structure and function of the bcl-6 gene in order to understand the pathogen consequences of chromosomal translocation of bcl-6 and its role in lymphomagenesis.

References

1. Gaidano, G., Dalla-Favera, R. Oncogenes and tumor suppressor genes. In: Neoplastic Hematopathology. D. M. Knowles (ed.). Wilkins & Wilkins (publ.), 245–261, 1992.
2. Dalla-Favera, R., Bregni, M., Erickson, J., Patterson, D., Gallo, R. C., and Croce, C. M. Human c-myc oncogene is located on the region of chromosome 8 that is translocated in Burkitt lymphoma cells. Proc. Natl. Acad. Sci. USA, 79:7824–7827, 1982.
3. Taub, R., Kirsch, I., Morton, C., Lenoir, G. M., Swan, D., Tronick, S., Aaronson, S., and Leder, P. Translocation of c-myc gene into the immunoglobulin heavy chain locus in human Burkitt lymphoma and murine plasmacytoma cells. Proc. Natl. Acad. Sci. USA, 79:7837–7841, 1982.
4. Bakhshi, A., Jensen, J. P., Goldman, P., Wright, J. J., McBride, O. W., Epstein, A. L., Korsmeyer, S. J. Cloning the chromosomal breakpoint of t(14;18) human lymphomas: clustering around $J_H$ on chromosome 14 and near a transcriptional unit on 18. Cell, 41:889–906, 1985.
5. Tsujimoto, U., Cossman, J., Jaffe, E., Croce, C. M. Involvement of the Bcl-2 gene in human follicular lymphoma. Science, 228:1440–1443, 1985.
6. Cleary, M. L., Sklar, J. Nucleotide sequence of a t(14;18) chromosomal breakpoint in follicular lymphoma and demonstration of a breakpoint-cluster region near a transcriptionally active locus on chromosome 18. Proc. Natl. Acad. Sci. USA, 82:7439–7444, 1985.
7. Motokura, T., Bloom T., Goo, K. H., Juppner, H., Ruderman, J. V., Kronenberg, H. M., Arnold, A. A novel cyclin encoded by a bcl-1 linked candidate oncogene. Nature, 350:512–514, 1991.
8. Raffeld, M., Jaffe, E. S. Bcl-1, t(11;14), and mantle zone lymphomas. Blood, 78:259–261, 1991.
9. Offit, K., Khanwar, S., Ebrahim, S. A. D., Filippa, D., Clarkson, B. D. and Chaganti, R. S. K. t(3;22)(q27;q11): A novel translocation associated with diffuse non-Hodgkin's lymphoma. Blood, 74:1876–1879, 1989.
10. Bastard, C., Tilly, H., Lenormand, B., Bigorgne, C., Boulet, D., Kunlin, A., Monconduit, M. and Piguet, H. Translocations involving band 3q37 and Ig gene regions in non-Hodgkin's lymphoma. Blood, 79:2527–2531, 1992.
11. Miller, S. A., Dykes, D. D. and Polesky, H. F. A simple salting out procedure for extracting DNA from human nucleated cells. Nucleic Acids Res., 16:1215–1218, 1988.
12. Feinberg, A. P. and Vogelstein, B. A technique for radiolabelling DNA restriction endonuclease fragments to high specific activity. Anal. Biochem., 132:6–13, 1983.
13. Ravetch, J. V., Siebenlist, U., Korsmeyer, S., Waldman, T., Leder, P. Structure of the human immunoglobulin μ locus: characterization of embryonic and rearranged J and D regions. Cell, 27:583–591, 1981.
14. Rao, P. H., Murty, V. V. V. S., Gaidano, G., Hauptschein, R., Dalla-Favera, R., Chaganti, R. S. K. Subregional localization of 20 single-copy loci to chromosome 6 by fluorescence in situ hybridization. Genomics, in press.
15. Chirgwin, J. M., Przybyla, A. E., MacDonald, R. J., Rutter, W. J. Isolation of biologically active ribonucleic acid from sources enriched in ribonuclease. Biochemistry, 18:5294–5299, 1979.
16. Peschle, C., Mavilio, F., Sposi, N. M., Gampaola, A., Care, A., Bottero, L., Bruno, M., Mastroberardino, G., Gastaldi, R., Testa, R., Alimena, M. G., Amadori, S., Mandelli, F. Translocation and rearrangement of c-myc into immunoglobulin alpha heavy chain locus in primary cells from acute lymphocytic leukemia. Proc. Natl. Acad. Sci. U.S.A., 81:5514–5518, 1984.
17. Showe, L. C., Ballantine, M., Nishikura, K., Erikson, J., Kaji, H., Croce, C. M. Cloning and sequencing of a c-myc oncogene in a Burkitt's lymphoma cell line that is translocated to a germ line alpha switch region. Mol. Cell. Biol., 5:501–509, 1985.
18. Neri, A., Barriga, F., Knowles, D. M., Magrath, I., Dalla-Favera, R. Different regions of the immunoglobulin heavy chain locus are involved in chromosomal translocations in distinct pathogenic forms of Burkitt lymphoma. Proc. Natl. Acad. Sci. USA, 85:2748–2752, 1988.
19. Rabbits, T. H., Forster, A., Milstein, C. P. Human immunoglobulin heavy chain genes: evolutionary comparisons of C mu, C delta and C gamma genes and associated switch sequences. Nucleic Acids Res., 9:4509–4524, 1981.
20. Schmid, et al. (1991) Nature, 332:733.

What is claimed is:

1. An isolated nucleic acid molecule having the nucleic acid sequence as set forth in SEQ ID NO.1.
2. A DNA molecule of claim 1.
3. A cDNA molecule of claim 2.
4. A genomic DNA molecule of claim 2.
5. An RNA molecule of claim 1.
6. A human nucleic acid molecule of claim 1.
7. An isolated nucleic acid molecule of at least 15 nucleotides which is complementary to a sequence of the isolated nucleic acid molecule of claim 1.
8. A DNA molecule of claim 7.
9. An RNA molecule of claim 7.
10. An isolated, vertebrate nucleic acid molecule of claim 3 operatively linked to a promoter of RNA transcription.
11. A vector which comprises the nucleic acid molecule of claim 2 or 10.
12. A plasmid comprising the vector of claim 11.
13. The plasmid of claim 12 designated pGB31 (ATCC Accession Number 75476).
14. The plasmid of claim 12 designated pGB3s (ATCC Accession Number 75477).
15. A host vector system for the production of a polypeptide encoded by the isolated nucleic acid molecule of claim 1, which comprises the vector of claim 11 in a suitable host cell.
16. A host vector system of claim 15, wherein the suitable host is a bacterial cell, insect cell, or animal cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3720 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 328..2445

( x i ) SEQUENCE DESCRIPTION: SEQ ID NO:1:

```
GGCCCCTCGA  GCCTCGAACC  GGAACCTCCA  AATCCGAGAC  GCTCTGCTTA  TGAGGACCTC      60

GAAATATGCC  GGCCAGTGAA  AAAATCTTAT  GGCTTTGAGG  GCTTTTGGTT  GGCCAGGGGC     120

AGTAAAAATC  TCGGAGAGCT  GACACCAAGT  CCTCCCCTGC  CACGTAGCAG  TGGTAAAGTC     180

CGAAGCTCAA  ATTCCGAGAA  TTGAGCTCTG  TTGATTCTTA  GAACTGGGGT  TCTTAGAAGT     240

GGTGATGCAA  GAAGTTTCTA  GGAAAGGCCG  GACACCAGGT  TTTGAGCAAA  ATTTTGGACT     300

GTGAAGCAAG  GCATTGGTGA  AGACAAA ATG GCC TCG CCG GCT GAC AGC TGT           351
                              Met Ala Ser Pro Ala Asp Ser Cys
                              1               5

ATC CAG TTC ACC CGC CAT GCC AGG GAT GTT CTT CTC AAC CTT AAT CGT           399
Ile Gln Phe Thr Arg His Ala Arg Asp Val Leu Leu Asn Leu Asn Arg
        10              15                  20

CTC CGG AGT CGA GAC ATC TTG ACT GAT GTT GTC ATT GTT GTG AGC CGT           447
Leu Arg Ser Arg Asp Ile Leu Thr Asp Val Val Ile Val Val Ser Arg
25              30                  35                  40

GAG CAG TTT AGA GCC CAT AAA ACG GTC CTC ATG GCC TGG AGA GGC CTG           495
Glu Gln Phe Arg Ala His Lys Thr Val Leu Met Ala Trp Arg Gly Leu
                45                  50                  55

TTC TAT AGC ATC TTT ACA GAC CAG TTG AAA TGC AAC CTT AGT GTG ATC           543
Phe Tyr Ser Ile Phe Thr Asp Gln Leu Lys Cys Asn Leu Ser Val Ile
                60                  65                  70

AAT CTA GAT CCT GAG ATC AAC CCT GAG GGA TTC TGC ATC CTC CTG GAC           591
Asn Leu Asp Pro Glu Ile Asn Pro Glu Gly Phe Cys Ile Leu Leu Asp
            75                  80                  85
```

| | | | | | | | | | | | | | | | | |
|---|---|---|---|---|---|---|---|---|---|---|---|---|---|---|---|---|
| TTC | ATG | TAC | ACA | TCT | CGG | CTC | AAT | TTG | CGG | GAG | GGC | AAC | ATC | ATG | GCT | 639 |
| Phe | Met | Tyr | Thr | Ser | Arg | Leu | Asn | Leu | Arg | Glu | Gly | Asn | Ile | Met | Ala | |
| | 90 | | | | 95 | | | | | 100 | | | | | | |
| GTG | ATG | GCC | ACG | GCT | ATG | TAC | CTG | CAG | ATG | GAG | CAT | GTT | GTG | GAC | ACT | 687 |
| Val | Met | Ala | Thr | Ala | Met | Tyr | Leu | Gln | Met | Glu | His | Val | Val | Asp | Thr | |
| 105 | | | | | 110 | | | | | 115 | | | | | 120 | |
| TGC | CGG | AAG | TTT | ATT | AAG | GCC | AGT | GAA | GCA | GAG | ATG | GTT | TCT | GCC | ATC | 735 |
| Cys | Arg | Lys | Phe | Ile | Lys | Ala | Ser | Glu | Ala | Glu | Met | Val | Ser | Ala | Ile | |
| | | | | 125 | | | | | 130 | | | | | 135 | | |
| AAG | CCT | CCT | CGT | GAA | GAG | TTC | CTC | AAC | AGC | CGG | ATG | CTG | ATG | CCC | CAA | 783 |
| Lys | Pro | Pro | Arg | Glu | Glu | Phe | Leu | Asn | Ser | Arg | Met | Leu | Met | Pro | Gln | |
| | | | 140 | | | | | 145 | | | | | 150 | | | |
| GAC | ATC | ATG | GCC | TAT | CGG | GGT | CGT | GAG | GTG | GTG | GAG | AAC | AAC | CTG | CCA | 831 |
| Asp | Ile | Met | Ala | Tyr | Arg | Gly | Arg | Glu | Val | Val | Glu | Asn | Asn | Leu | Pro | |
| | | 155 | | | | | 160 | | | | | 165 | | | | |
| CTG | AGG | AGC | GCC | CCT | GGG | TGT | GAG | AGC | AGA | GCC | TTT | GCC | CCC | AGC | CTG | 879 |
| Leu | Arg | Ser | Ala | Pro | Gly | Cys | Glu | Ser | Arg | Ala | Phe | Ala | Pro | Ser | Leu | |
| | 170 | | | | | 175 | | | | | 180 | | | | | |
| TAC | AGT | GGC | CTG | TCC | ACA | CCG | CCA | GCC | TCT | TAT | TCC | ATG | TAC | AGC | CAC | 927 |
| Tyr | Ser | Gly | Leu | Ser | Thr | Pro | Pro | Ala | Ser | Tyr | Ser | Met | Tyr | Ser | His | |
| 185 | | | | | 190 | | | | | 195 | | | | | 200 | |
| CTC | CCT | GTC | AGC | AGC | CTC | CTC | TTC | TCC | GAT | GAG | GAG | TTT | CGG | GAT | GTC | 975 |
| Leu | Pro | Val | Ser | Ser | Leu | Leu | Phe | Ser | Asp | Glu | Glu | Phe | Arg | Asp | Val | |
| | | | | 205 | | | | | 210 | | | | | 215 | | |
| CGG | ATG | CCT | GTG | GCC | AAC | CCC | TTC | CCC | AAG | GAG | CGG | GCA | CTC | CCA | TGT | 1023 |
| Arg | Met | Pro | Val | Ala | Asn | Pro | Phe | Pro | Lys | Glu | Arg | Ala | Leu | Pro | Cys | |
| | | | 220 | | | | | 225 | | | | | 230 | | | |
| GAT | AGT | GCC | AGG | CCA | GTC | CCT | GGT | GAG | TAC | AGC | CGG | CCG | ACT | TTG | GAG | 1071 |
| Asp | Ser | Ala | Arg | Pro | Val | Pro | Gly | Glu | Tyr | Ser | Arg | Pro | Thr | Leu | Glu | |
| | | 235 | | | | | 240 | | | | | 245 | | | | |
| GTG | TCC | CCC | AAT | GTG | TGC | CAC | AGC | AAT | ATC | TAT | TCA | CCC | AAG | GAA | ACA | 1119 |
| Val | Ser | Pro | Asn | Val | Cys | His | Ser | Asn | Ile | Tyr | Ser | Pro | Lys | Glu | Thr | |
| | 250 | | | | | 255 | | | | | 260 | | | | | |
| ATC | CCA | GAA | GAG | GCA | CGA | AGT | GAT | ATG | CAC | TAC | AGT | GTG | GCT | GAG | GGC | 1167 |
| Ile | Pro | Glu | Glu | Ala | Arg | Ser | Asp | Met | His | Tyr | Ser | Val | Ala | Glu | Gly | |
| 265 | | | | | 270 | | | | | 275 | | | | | 280 | |
| CTC | AAA | CCT | GCT | GCC | CCC | TCA | GCC | CGA | AAT | GCC | CCC | TAC | TTC | CCT | TGT | 1215 |
| Leu | Lys | Pro | Ala | Ala | Pro | Ser | Ala | Arg | Asn | Ala | Pro | Tyr | Phe | Pro | Cys | |
| | | | | 285 | | | | | 290 | | | | | 295 | | |
| GAC | AAG | GCC | AGC | AAA | GAA | GAA | GAG | AGA | CCC | TCC | TCG | AAA | GAT | GAG | ATT | 1263 |
| Asp | Lys | Ala | Ser | Lys | Glu | Glu | Glu | Arg | Pro | Ser | Ser | Glu | Asp | Glu | Ile | |
| | | | 300 | | | | | 305 | | | | | 310 | | | |
| GCC | CTG | CAT | TTC | GAG | CCC | CCC | AAT | GCA | CCC | CTG | AAC | CGG | AAG | GGT | CTG | 1311 |
| Ala | Leu | His | Phe | Glu | Pro | Pro | Asn | Ala | Pro | Leu | Asn | Arg | Lys | Gly | Leu | |
| | | 315 | | | | | 320 | | | | | 325 | | | | |
| GTT | AGT | CCA | CAG | AGC | CCC | CAG | AAA | TCT | GAC | TGC | CAG | CCC | AAC | TCG | CCC | 1359 |
| Val | Ser | Pro | Gln | Ser | Pro | Gln | Lys | Ser | Asp | Cys | Gln | Pro | Asn | Ser | Pro | |
| | 330 | | | | | 335 | | | | | 340 | | | | | |
| ACA | GAG | GCC | TGC | AGC | AGT | AAG | AAT | GCC | TGC | ATC | CTC | CAG | GGT | TCT | GGC | 1407 |
| Thr | Glu | Ala | Cys | Ser | Ser | Lys | Asn | Ala | Cys | Ile | Leu | Gln | Gly | Ser | Gly | |
| 345 | | | | | 350 | | | | | 355 | | | | | 360 | |
| TCC | CCT | CCA | GCC | AAG | AGC | CCC | ACT | GAC | CCC | AAA | GCC | TGC | AGC | TGG | AAG | 1455 |
| Ser | Pro | Pro | Ala | Lys | Ser | Pro | Thr | Asp | Pro | Lys | Ala | Cys | Ser | Trp | Lys | |
| | | | | 365 | | | | | 370 | | | | | 375 | | |
| AAA | TAC | AAG | TTC | ATC | GTG | CTC | AAC | AGC | CTC | AAC | CAG | AAT | GCC | AAA | CCA | 1503 |
| Lys | Tyr | Lys | Phe | Ile | Val | Leu | Asn | Ser | Leu | Asn | Gln | Asn | Ala | Lys | Pro | |
| | | | 380 | | | | | 385 | | | | | 390 | | | |
| GGG | GGG | CCT | GAG | CAG | GCT | GAG | CTG | GGC | CGC | CTT | TCC | CCA | CGA | GCC | TAC | 1551 |
| Gly | Gly | Pro | Glu | Gln | Ala | Glu | Leu | Gly | Arg | Leu | Ser | Pro | Arg | Ala | Tyr | |
| | 395 | | | | | 400 | | | | | 405 | | | | | |

```
ACG GCC CCA CCT GCC TGC CAG CCA CCC ATG GAG CCT GAG AAC CTT GAC      1599
Thr Ala Pro Pro Ala Cys Gln Pro Pro Met Glu Pro Glu Asn Leu Asp
    410             415             420

CTC CAG TCC CCA ACC AAG CTG AGT GCC AGC GGG GAG GAC TCC ACC ATC      1647
Leu Gln Ser Pro Thr Lys Leu Ser Ala Ser Gly Glu Asp Ser Thr Ile
425             430             435                         440

CCA CAA GCC AGC CGG CTC AAT AAC ATC GTT AAC AGG TCC ATG ACG GGC      1695
Pro Gln Ala Ser Arg Leu Asn Asn Ile Val Asn Arg Ser Met Thr Gly
                445             450             455

TCT CCC CGC AGC AGC AGC GAG AGC CAC TCA CCA CTC TAC ATG CAC CCC      1743
Ser Pro Arg Ser Ser Ser Glu Ser His Ser Pro Leu Tyr Met His Pro
        460             465             470

CCG AAG TGC ACG TCC TGC GGC TCT CAG TCC CCA CAG CAT GCA GAG ATG      1791
Pro Lys Cys Thr Ser Cys Gly Ser Gln Ser Pro Gln His Ala Glu Met
        475             480             485

TGC CTC CAC ACC GCT GGC CCC ACG TTC GCT GAG GAG ATG GGA GAG ACC      1839
Cys Leu His Thr Ala Gly Pro Thr Phe Ala Glu Glu Met Gly Glu Thr
    490             495             500

CAG TCT GAG TAC TCA GAT TCT AGC TGT GAG AAC GGG GCC TTC TTC TGC      1887
Gln Ser Glu Tyr Ser Asp Ser Ser Cys Glu Asn Gly Ala Phe Phe Cys
505             510             515             520

AAT GAG TGT GAC TGC CGC TTC TCT GAG GAG GCC TCA CTC AAG AGG CAC      1935
Asn Glu Cys Asp Cys Arg Phe Ser Glu Glu Ala Ser Leu Lys Arg His
                525             530             535

ACG CTG CAG ACC CAC AGT GAC AAA CCC TAC AAG TGT GAC CGC TGC CAG      1983
Thr Leu Gln Thr His Ser Asp Lys Pro Tyr Lys Cys Asp Arg Cys Gln
            540             545             550

GCC TCC TTC CGC TAC AAG GGC AAC CTC GCC AGC CAC AAG ACC GTC CAT      2031
Ala Ser Phe Arg Tyr Lys Gly Asn Leu Ala Ser His Lys Thr Val His
        555             560             565

ACC GGT GAG AAA CCC TAT CGT TGC AAC ATC TGT GGG GCC CAG TTC AAC      2079
Thr Gly Glu Lys Pro Tyr Arg Cys Asn Ile Cys Gly Ala Gln Phe Asn
    570             575             580

CGG CCA GCC AAC CTG AAA ACC CAC ACT CGA ATT CAC TCT GGA GAG AAG      2127
Arg Pro Ala Asn Leu Lys Thr His Thr Arg Ile His Ser Gly Glu Lys
585             590             595             600

CCC TAC AAA TGC GAA ACC TGC GGA GCC AGA TTT GTA CAG GTG GCC CAC      2175
Pro Tyr Lys Cys Glu Thr Cys Gly Ala Arg Phe Val Gln Val Ala His
                605             610             615

CTC CGT GCC CAT GTG CTT ATC CAC ACT GGT GAG AAG CCC TAT CCC TGT      2223
Leu Arg Ala His Val Leu Ile His Thr Gly Glu Lys Pro Tyr Pro Cys
            620             625             630

GAA ATC TGT GGC ACC CGT TTC CGG CAC CTT CAG ACT CTG AAG AGC CAC      2271
Glu Ile Cys Gly Thr Arg Phe Arg His Leu Gln Thr Leu Lys Ser His
        635             640             645

CTG CGA ATC CAC ACA GGA GAG AAA CCT TAC CAT TGT GAG AAG TGT AAC      2319
Leu Arg Ile His Thr Gly Glu Lys Pro Tyr His Cys Glu Lys Cys Asn
    650             655             660

CTG CAT TTC CGT CAC AAA AGC CAG CTG CGA CTT CAC TTG CGC CAG AAG      2367
Leu His Phe Arg His Lys Ser Gln Leu Arg Leu His Leu Arg Gln Lys
665             670             675             680

CAT GGC GCC ATC ACC AAC ACC AAG GTG CAA TAC CGC GTG TCA GCC ACT      2415
His Gly Ala Ile Thr Asn Thr Lys Val Gln Tyr Arg Val Ser Ala Thr
                685             690             695

GAC CTG CCT CCG GAG CTC CCC AAA GCC TGC TGAAGCATGG AGTGTTGATG        2465
Asp Leu Pro Pro Glu Leu Pro Lys Ala Cys
            700             705

CTTTCGTCTC CAGCCCCTTC TCAGAATCTA CCCAAAGGAT ACTGTAACAC TTTACAATGT   2525

TCATCCCATG ATGTAGTGCC TCTTTCATCC ACTAGTGCAA ATCATAGCTG GGGGTTGGGG   2585
```

```
GTGGTGGGGG TCGGGGCCTG GGGGACTGGG AGCCGCAGCA GCTCCCCCTC CCCCACTGCC    2645
ATAAACATT  AAGAAAATCA TATTGCTTCT TCTCCTATGT GNNNNNNNNN NNNNNNNNNN    2705
NNNNNNNNNN NNNNNNNNNN NNNNNNNNNN NNNNNNNNNN NNNNNNNNNN NNNNNNNNNN    2765
NNNNNNNNNN NNNNNNNNNN NNNNNNNNNN NNNNNNNNNN NNNNNNNNNN NNNNNNNNNN    2825
NNNNNNNNNN NNNNNNNNNN NNNNNNNNNN NNNNNNNNNN NNNNNNNNNN NNNNNNNNNN    2885
NNNNNNNNNN NNNNNNNNNN NNNNNNNNNN NNNNNNNNNN NNNNNNNNNN NNNNNNNNNN    2945
NNNNNNNNNN NNNNNNNNNN NNNNNNNNNN NNNNNNNNNN NNNNNNNNNN NNNNNNNNNN    3005
NNNNNNNNNN NNNNNNNNNN NNNNNNNNNN NNNNNNNNNN NNNNNNNNNN NNNNNNNNNN    3065
NNNNNNNNNN NNNNNNNNNN NNNNNNNNNN NNNNNNNNNN NNNNNNNNNN NNNNNNNNNN    3125
NNNNNNNNNN NNNNNNNNNN NNNNNNNNNN NNNNNNNNNN NNNNNNNNNN NNNNNNNNNN    3185
NNNNNNNNNN NNNNNNNNNN NNNNNNNNNN NNNNNNNNNN NNNNNNNNNN NNNNNNNNNN    3245
NTTTAAGTAT TGCATCTGTA TAAGTAAGAA AATATTTTGT CTAAAATGCC TCAGTGTATT    3305
TGTATTTTTT TGCAAGTGGG GGGTTACAAT TTACCCAGTG TGTATTAAAA AAAACCCAAA    3365
GAACCCAAAA ATCTCCAGAA GGAAAAATGT GTAATTTTGT TCTAGTTTTC AGTTTGTATA    3425
TACCCGTACA ACGTGTCCTC ACGGTGCCTT TTTTCACGGA AGTTTTCAAT GATGGGCGAG    3485
CGTGCACCAT CCCTTTTTGA AGTGTAGGCA GACACAGGGA CTTGAAGTTG TTACTAACTA    3545
AACTCTCTTT GGGAATGTTT GTCTCATCCC ANTCTGCGTC ATGCTTGTGT GATAACTACT    3605
CCGGAGACAG GGTTTGGCTG TGTCTAAACT GCATTACCGC GTTGTAAAAA ATAGCTGTAC    3665
CAATATAAGA ATAAATGTT  GGAAAGTCGC AAAAAAAAAA AAAAAAAAAA AAAAA         3720
```

( 2 ) INFORMATION FOR SEQ ID NO:2:

( i ) SEQUENCE CHARACTERISTICS:
        ( A ) LENGTH: 706 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ser Pro Ala Asp Ser Cys Ile Gln Phe Thr Arg His Ala Arg
 1               5                  10                  15

Asp Val Leu Leu Asn Leu Asn Arg Leu Arg Ser Arg Asp Ile Leu Thr
                20                  25                  30

Asp Val Val Ile Val Val Ser Arg Glu Gln Phe Arg Ala His Lys Thr
            35                  40                  45

Val Leu Met Ala Trp Arg Gly Leu Phe Tyr Ser Ile Phe Thr Asp Gln
 50                  55                  60

Leu Lys Cys Asn Leu Ser Val Ile Asn Leu Asp Pro Glu Ile Asn Pro
 65                  70                  75                  80

Glu Gly Phe Cys Ile Leu Leu Asp Phe Met Tyr Thr Ser Arg Leu Asn
                85                  90                  95

Leu Arg Glu Gly Asn Ile Met Ala Val Met Ala Thr Ala Met Tyr Leu
               100                 105                 110

Gln Met Glu His Val Val Asp Thr Cys Arg Lys Phe Ile Lys Ala Ser
           115                 120                 125

Glu Ala Glu Met Val Ser Ala Ile Lys Pro Pro Arg Glu Glu Phe Leu
130                 135                 140

Asn Ser Arg Met Leu Met Pro Gln Asp Ile Met Ala Tyr Arg Gly Arg
145                 150                 155                 160
```

```
Glu  Val  Val  Glu  Asn  Asn  Leu  Pro  Leu  Arg  Ser  Ala  Pro  Gly  Cys  Glu
               165                      170                      175

Ser  Arg  Ala  Phe  Ala  Pro  Ser  Leu  Tyr  Ser  Gly  Leu  Ser  Thr  Pro  Pro
               180                      185                      190

Ala  Ser  Tyr  Ser  Met  Tyr  Ser  His  Leu  Pro  Val  Ser  Ser  Leu  Leu  Phe
               195                      200                      205

Ser  Asp  Glu  Glu  Phe  Arg  Asp  Val  Arg  Met  Pro  Val  Ala  Asn  Pro  Phe
          210                      215                      220

Pro  Lys  Glu  Arg  Ala  Leu  Pro  Cys  Asp  Ser  Ala  Arg  Pro  Val  Pro  Gly
225                           230                 235                      240

Glu  Tyr  Ser  Arg  Pro  Thr  Leu  Glu  Val  Ser  Pro  Asn  Val  Cys  His  Ser
               245                      250                      255

Asn  Ile  Tyr  Ser  Pro  Lys  Glu  Thr  Ile  Pro  Glu  Glu  Ala  Arg  Ser  Asp
               260                      265                      270

Met  His  Tyr  Ser  Val  Ala  Glu  Gly  Leu  Lys  Pro  Ala  Ala  Pro  Ser  Ala
               275                      280                      285

Arg  Asn  Ala  Pro  Tyr  Phe  Pro  Cys  Asp  Lys  Ala  Ser  Lys  Glu  Glu  Glu
          290                      295                 300

Arg  Pro  Ser  Ser  Glu  Asp  Glu  Ile  Ala  Leu  His  Phe  Glu  Pro  Pro  Asn
305                           310                 315                      320

Ala  Pro  Leu  Asn  Arg  Lys  Gly  Leu  Val  Ser  Pro  Gln  Ser  Pro  Gln  Lys
                    325                      330                      335

Ser  Asp  Cys  Gln  Pro  Asn  Ser  Pro  Thr  Glu  Ala  Cys  Ser  Ser  Lys  Asn
               340                      345                      350

Ala  Cys  Ile  Leu  Gln  Gly  Ser  Gly  Ser  Pro  Pro  Ala  Lys  Ser  Pro  Thr
               355                      360                      365

Asp  Pro  Lys  Ala  Cys  Ser  Trp  Lys  Lys  Tyr  Lys  Phe  Ile  Val  Leu  Asn
370                           375                      380

Ser  Leu  Asn  Gln  Asn  Ala  Lys  Pro  Gly  Gly  Pro  Glu  Gln  Ala  Glu  Leu
385                      390                      395                      400

Gly  Arg  Leu  Ser  Pro  Arg  Ala  Tyr  Thr  Ala  Pro  Pro  Ala  Cys  Gln  Pro
                    405                      410                      415

Pro  Met  Glu  Pro  Glu  Asn  Leu  Asp  Leu  Gln  Ser  Pro  Thr  Lys  Leu  Ser
               420                      425                      430

Ala  Ser  Gly  Glu  Asp  Ser  Thr  Ile  Pro  Gln  Ala  Ser  Arg  Leu  Asn  Asn
          435                      440                      445

Ile  Val  Asn  Arg  Ser  Met  Thr  Gly  Ser  Pro  Arg  Ser  Ser  Ser  Glu  Ser
450                      455                      460

His  Ser  Pro  Leu  Tyr  Met  His  Pro  Pro  Lys  Cys  Thr  Ser  Cys  Gly  Ser
465                      470                      475                      480

Gln  Ser  Pro  Gln  His  Ala  Glu  Met  Cys  Leu  His  Thr  Ala  Gly  Pro  Thr
               485                      490                      495

Phe  Ala  Glu  Glu  Met  Gly  Glu  Thr  Gln  Ser  Glu  Tyr  Ser  Asp  Ser  Ser
          500                      505                      510

Cys  Glu  Asn  Gly  Ala  Phe  Phe  Cys  Asn  Glu  Cys  Asp  Cys  Arg  Phe  Ser
          515                      520                      525

Glu  Glu  Ala  Ser  Leu  Lys  Arg  His  Thr  Leu  Gln  Thr  His  Ser  Asp  Lys
          530                      535                      540

Pro  Tyr  Lys  Cys  Asp  Arg  Cys  Gln  Ala  Ser  Phe  Arg  Tyr  Lys  Gly  Asn
545                      550                      555                      560

Leu  Ala  Ser  His  Lys  Thr  Val  His  Thr  Gly  Glu  Lys  Pro  Tyr  Arg  Cys
               565                      570                      575

Asn  Ile  Cys  Gly  Ala  Gln  Phe  Asn  Arg  Pro  Ala  Asn  Leu  Lys  Thr  His
```

-continued

|  |  |  |  |  |  |  | 580 |  |  |  |  |  | 585 |  |  |  |  |  | 590 |  |  |  |
|---|---|---|---|---|---|---|---|---|---|---|---|---|---|---|---|---|---|---|---|---|---|---|
| Thr | Arg | Ile 595 | His | Ser | Gly | Glu | Lys 600 | Pro | Tyr | Lys | Cys | Glu 605 | Thr | Cys | Gly |
| Ala | Arg 610 | Phe | Val | Gln | Val | Ala 615 | His | Leu | Arg | Ala | His 620 | Val | Leu | Ile | His |
| Thr 625 | Gly | Glu | Lys | Pro | Tyr 630 | Pro | Cys | Glu | Ile | Cys 635 | Gly | Thr | Arg | Phe | Arg 640 |
| His | Leu | Gln | Thr | Leu 645 | Lys | Ser | His | Leu | Arg 650 | Ile | His | Thr | Gly | Glu 655 | Lys |
| Pro | Tyr | His | Cys 660 | Glu | Lys | Cys | Asn | Leu 665 | His | Phe | Arg | His 670 | Lys | Ser | Gln |
| Leu | Arg | Leu 675 | His | Leu | Arg | Gln | Lys 680 | His | Gly | Ala | Ile | Thr 685 | Asn | Thr | Lys |
| Val | Gln 690 | Tyr | Arg | Val | Ser | Ala 695 | Thr | Asp | Leu | Pro | Pro 700 | Glu | Leu | Pro | Lys |
| Ala 705 | Cys | | | | | | | | | | | | | | |